Sept. 4, 1962 D. L. ARMSTRONG ET AL Plant Pat. 2,170
ROSE PLANT
Filed Oct. 9, 1961
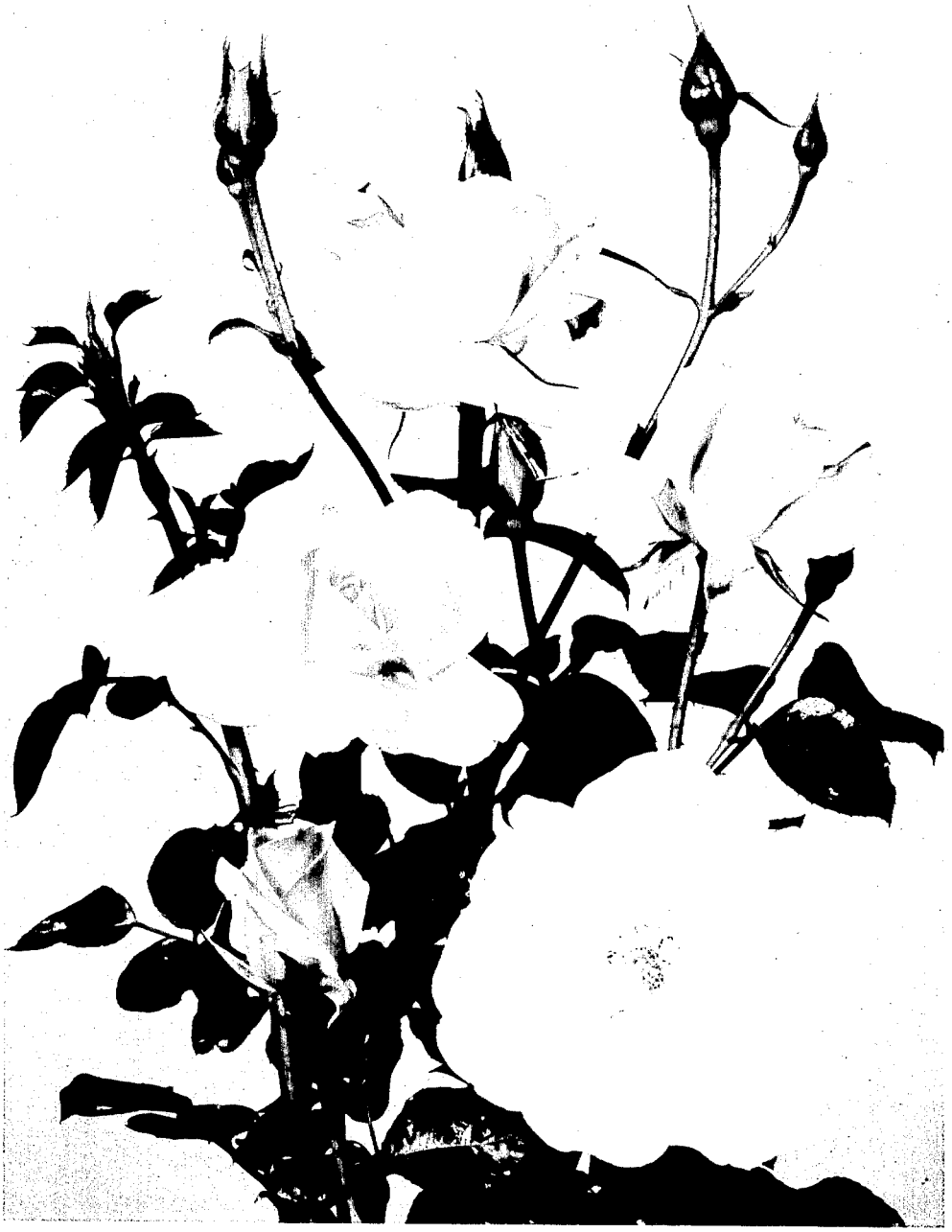
Inventors.
David L. Armstrong
Herbert C. Swim
By: Robb & Robb
Attorneys.

United States Patent Office

Plant Pat. 2,170
Patented Sept. 4, 1962

2,170
ROSE PLANT

David L. Armstrong and Herbert C. Swim, Ontario, Calif., assignors to Armstrong Nurseries, Inc., Ontario, Calif., a corporation of California Filed Oct. 9, 1961, Ser. No. 144,015
1 Claim. (Cl. 47—61)

The present invention relates to a new and distinct variety of rose plant of the hybrid tea class, which was originated by us by crossing the variety "La Jolla" (Plant Patent No. 1,103) with an unnamed and unpatented seedling of unidentified parentage, the latter variety being the pollen parent and the variety "La Jolla" being the seed parent.

The unnamed pollen parent is a variety of the hybrid tea class, which is characterized by a very vigorous habit of plant growth, a habit of bearing flowers on very long, single stems, with the buds being very long and urn-shaped in form and which open into medium pink flowers of semi-double petalage, but having a rather shapeless and irregular open flower form. This latter fault has made this particular variety unsuitable for commercial use, but because of the fact that it has other good features, it has proved to be useful for breeding purposes.

The general objective of this particular breeding was to produce an improved hybrid tea type of rose which bears flowers in the pink or pink blend color range, while at the same time combining the large glossy foliage, the quite double petalage, and the good bud and flower form of the parent variety "La Jolla," with the greater vigor, longer stems, and long urn-shaped buds of semi-double petalage of the unnamed pollen parent, thereby achieving a new rose variety of an attractive pink flower color, with long, urn-shaped buds of at least medium or greater petalage, together with long stems and good vigor. These objectives were substantially achieved, along with other desirable improvements, as evidenced by the following unique combination of characteristics which distinguish the new variety from its parents, as well as from all other varieties of which we are aware:

(1) A relatively upright plant habit;

(2) A vigor that is considerably greater than that of the average hybrid tea rose variety;

(3) Attractive, dark green, relatively glossy foliage;

(4) A very floriferous habit;

(5) A habit of bearing flowers usually on single stems of medium length, but also often in small clusters of from 2 to 5 flowers where the shoots are quit vigorous;

(6) A moderately double flower form having an excellent urn-shape in the bud stage and an attractive open flower form and a size comparable to the average hybrid tea roses; and (7) An attractive and distinctive general color tonality of the flowers corresponding to between Dawn Pink and Camellia Rose in the newly open flower stage, with the reverse face of the petals being more red and generally ranging between Tyrian Rose and Rose Bengal, the colors becoming lighter on the inner surface of the petals as the flowers age.

In comparison with its seed parent, "La Jolla," the flower of the new variety has considerably less petalage, and the flower color is a pink bi-color, as distinguished from the multi-colored pink and yellow tones of the flowers of "La Jolla."

As compared with its unnamed pollen parent, the new variety is somewhat less vigorous, has shorter stems and tends to bear flowers in clusters considerably more than occurs in this parent, the flowers have more petals than the only semi-double petalage of the flowers of this parent, while the flowers are of better form in the open stage and are a bi-color pink, with darker reverse in contrast to the medium pink color throughout the flower of the parent variety.

Asexual reproduction of our new variety by budding, as performed at Ontario, California, shows that the foregoing characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Outdoor; seedling; for cut flowers and for garden decoration.

Class: Hybrid tea.

Breeding: Seedling.

*Seed parent.*—"La Jolla."

*Pollen parent.*—An unnamed seedling variety of unidentified parentage.

Propagation: Holds its distinguishing characteristics through succeeding propagations by budding.

*Flower*

Locality where grown and observed: Ontario, California.

Flowers borne: Usually singly, but sometimes from 2 to 5 to stem; in irregular cluster; on from medium to long stems of normal strength.

Quantity of bloom: Free, outdoors.

Continuity: Nearly continuous during growing season.

Fragrance: Slight.

Bud:

*Peduncle.*—Average length; average caliper; erect; usually smooth; with from few to several small stipitate glands and from several to many small prickles. Color—between Apple Green, Plate XVII (Ridgway) and Courge Green, Plate XVII (Ridgway), overlaid with near Yellowish Oil Green, Plate V (Ridgway) on side exposed to sun.

*Before calyx breaks.*—Size—from small to medium. Form—from short to medium length; ovoid.

*As calyx breaks.*—Color—between Claret Rose, Plate 021, page 109 (Wilson) and Cardinal Red, Plate 822/1, page 168 (Wilson).

*Sepals.*—Inner surface—with fine, wooly tomentum. Outer surface—usually smooth. Alternate margins—lined with fine, wooly tomentum. Other margins—lined with from few to several small stipitate glands and small, slender, foliaceous parts.

*As first petal opens.*—Size—average. Form—medium length; from ovoid to urn-shaped. Color: outside—between Crimson, Plate 22/1, page 22 (Wilson) and Rose Madder, Plate 23, page 23 (Wilson), with small area at base near attachment near Sulphur Yellow, Plate 1/2, page 1 (Wilson); inside—between French Rose, Plate 520/1, page 136 (Wilson) and Dawn Pink, Plate 523/1, page 137 (Wilson), with small area at base near attachment near Sulphur Yellow, Plate 1/2, page 1 (Wilson).

*Opening.*—Opens up well; is not retarded or prevented from opening by cold, hot, wet or dry weather.

Bloom:

*Size (when fully open).*—Average; from 3½ inches to 4 inches.

*Petalage.*—Double; from 24 to 30 petals, plus 6 to 8 petaloids; arranged irregularly.

*Form.*—High-centered at first, but becoming from cupped to high-centered; petals being at first tightly cupped, with tips reflexed slightly outward, but later becoming more loosely cupped, with tips reflexed outwardly at maturity; outer and intermediate petals of both newly opened and three-days open flowers usually reflexed slightly outward both along edges and apex of petals.

Petals:

*Texture.*—Medium thickness. Inside—satiny. Outside—satiny.

*Shape.*—Outside—broadly obovate, with apex flat, and sometimes with from 1 to 3 notches. Intermediate—obovate, with apex from rounded to flat, and sometimes with from 1 to 3 notches. Inside—obovate, with apex rounded.

This description of a newly opened flower was made from a rose grown outdoors during the month of June at Ontario, California:

*Color.*—Outer petal: outside surface—between Tyrian Rose, Plate 24/2, page 24 (Wilson) and Rose Bengal, Plate 25/3, page 25 (Wilson), with small area at base near attachment near Sulphur Yellow, Plate 1/3, page 1 (Wilson); inside surface—between Rhodamine Pink, Plate 527/2, page 138 (Wilson) and Camellia Rose, Plate 622/3, page 148 (Wilson), with small area at base near attachment near Sulphur Yellow, Plate 1/3, page 1 (Wilson). Intermediate petal: outside surface—between Tyrian Rose, Plate 24/2, page 24 (Wilson) and Rose Bengal, Plate 25/3, page 25 (Wilson), with small area at base near attachment near Sulphur Yellow, Plate 1/3, page 1 (Wilson); Inside surface—between Dawn Pink, Plate 523/2, page 137 (Wilson) and Camellia Rose, Plate 622/3, page 148 (Wilson), with small area at base near attachment near Sulphur Yellow, Plate 1/3, page 1 (Wilson). Inner petal: outside surface—between Rose Madder, Plate 23/2, page 23 (Wilson) and Tyrian Rose, Plate 24/2, page 24 (Wilson), with small area at base near attachment near Sulphur Yellow, Plate 1/3, page 1 (Wilson); inside surface—between Dawn Pink, Plate 523/1, page 137 (Wilson) and Camellia Rose, Plate 622/2, page 148 (Wilson), with small area at base near attachment near Sulphur Yellow, Plate 1/3, page 1 (Wilson).

This description was made from a rose that was open for 3 days outdoors during the month of June at Ontario, California:

*Color.*—Outer petal: outside surface—between Solferino Purple, Plate 26/2, page 26 (Wilson) and Magenta, Plate 27/2, page 27 (Wilson), with small area at base near attachment near Canary Yellow, Plate 2/3, page 2 (Wilson); inside surface—between Rhodamine Pink, Plate 527/3, page 138 (Wilson) and Amaranth Rose, Plate 530/3, page 139 (Wilson), with small area at base near Canary Yellow, Plate 2/3, page 2 (Wilson). Inner petal: outside surface—between Solferino Purple, Plate 26/3, page 26 (Wilson) and Magenta, Plate 27/3, page 27 (Wilson), with small area at base near attachment near Canary Yellow, Plate 2/3, page 2 (Wilson); inside surface—between Rose Pink, Plate 427/3, page 126 (Wilson) and Rhodamine Pink, Plate 527/3, page 138 (Wilson), with small area at base near Canary Yellow, Plate 2/3, page 2 (Wilson).

*General color effect.*—Newly opened flower—between Dawn Pink, Plate 523/2, page 137 (Wilson) and Camellia Rose, Plate 622/3, page 148 (Wilson). 3-days open—between Rose Pink, Plate 427/2, page 126 (Wilson) and Rhodamine Pink, Plate 527/3, page 138 (Wilson).

*Behavior.*—Drop off cleanly; not particularly affected by cold, hot, wet or dry weather.

*Flower longevity.*—On bush in garden—4 or 5 days in June. Cut roses grown outdoors and kept at living-room temperatures—5 or 6 days in June.

*Reproductive Organs*

Stamens: Average number; arranged regularly about pistils; a few mixed with petaloids.

Filaments: From short to medium length (from 4 to 10 mm.); most with anthers. Color—near Canary Yellow, Plate 2/2, page 2 (Wilson).

Anthers: From small to medium size; all open approximately at once. Color: upper side—margins near Majolica Yellow, Plate 09/1, page 102 (Wilson), with remainder near Amber Yellow, Plate 505/2, page 132 (Wilson); under side—margins near Majolica Yellow, Plate 09/1, page 102 (Wilson), with remainder near Amber Yellow, Plate 505/2, page 132 (Wilson).

Pollen: Moderate quantity. Color—near Cadmium Orange, Plate 8/1, page 8 (Wilson).

Pistils: Average number (approximately 80).

Styles: Uneven; from short to average length (from 3 to 10 mm.); thin; bunched. Color—upper half near Crimson, Plate 22, page 22 (Wilson), with remainder near Sulphur Yellow, Plate 1/3, page 1 (Wilson).

Stigma: Color—near Chinese Yellow, Plate 606/2, page 68 (Wilson).

Ovaries: Usually all enclosed in calyx.

Hips: From short to average length; globular; smooth; walls thick and fleshy. Color (half mature)—near Courge Green, Plate XVII (Ridgway).

Sepals: Falling soon; medium length; straight. Color: inside—near Grape Green, Plate XLI (Ridgway); outside—near Courge Green, Plate XVII (Ridgway).

Seeds: From few to average number (from 12 to 18); usually small.

*Plant*

Foliage:

*Leaves.*—Compound of usually 3–7 leaflets; normal abundance; medium size; leathery; semi-glossy.

*Leaflets.*—Shape—between oval and oblong, with apex acute. Base—round. Margin—doubly serrate.

*Color.*—Mature: upper surface—between Forest Green, Plate XVII (Ridgway) and Empire Green, Plate XXXII (Ridgway); under surface—near Biscay Green, Plate XVII (Ridgway). Young: upper surface—between Dark Corinthian Purple, Plate XXXVIII (Ridgway) and Olive Brown, Plate XL (Ridgway); under surface—near Sorghum Brown, Plate XXXIX (Ridgway).

*Rachis (the supporting stem of the compound leaf).*—Average size. Upper side—grooved; with from few to several stipitate glands on edges. Under side—smooth; with from none to few small prickles.

*Stipules.*—Short; from narrow to medium width; with short points turning out at an angle of less than 45°.

*Disease resistance.*—Better than average resistance to mildew as compared to other varieties grown under comparable cultural conditions at Ontario, California.

Growth:

*Habit.*—Bushy; upright; somewhat spreading; much-branched.

*Growth.*—Very vigorous.

*Canes.*—From medium caliper to heavy.

*Main stems.*—Color—near light Elm Green, Plate XVII (Ridgway). Large prickles—from several to many; mediu mlength; almost straight; with narrow base of medium length; color—near Orange-Cinnamon, Plate XXIX (Ridgway). Small prickles—very few; color—near Orange-Cinnamon, Plate XXIX (Ridgway). Hairs—none.

*Branches.*—Color—near Biscay Green, Plate XVII (Ridgway). Large prickles—from several to many; from short to medium length; almost straight; with narrow base of from short to medium length; color—near Army Brown, Plate XL (Ridgway). Small prickles—few; color—near Army Brown, Plate XL (Ridgway).

*New shoots.*—Color—near Serpentine Green, Plate XVI (Ridgway). Large prickles—from few to several; from short to medium length; almost straight; with narrow base of from short to medium length; color—near Deep Corinthian Red, Plate XXVII (Ridgway). Small prickles—few;

color—near Deep Corinthian Red, Plate XXVII (Ridgway). Hairs—none.

We claim:

A new and distinct variety of rose plant of the hybrid tea class, substantially as herein shown and described, characterized particularly as to novelty by the unique combination of a relatively upright and vigorous habit of growth, attractive dark green and relatively glossy foliage, a very floriferous habit, a habit of bearing flowers usually singly and on stems of medium length, but also often in small clusters where shoots are quite vigorous, a moderately double flower form having an excellent urn-shape in the bud stage and having an attractive open flower form, said flowers being of average size, and a distinctive and attractive general color tonality in the newly opened flower stage ranging between Dawn Pink and Camellia Rose, with the reverse surfaces of the petals being more red and generally ranging between Tyrian Rose and Rose Bengal, the color on the inside surfaces of the petals becoming lighter with age.

No references cited.